(12) United States Patent
Bayne

(10) Patent No.: US 7,249,036 B2
(45) Date of Patent: Jul. 24, 2007

(54) METHOD FOR CLINICIAN HOUSE CALLS UTILIZING PORTABLE COMPUTING AND COMMUNICATIONS EQUIPMENT

(75) Inventor: C. Gresham Bayne, San Diego, CA (US)

(73) Assignee: Cary Gresham Bayne, San Diego, CA (US)

( * ) Notice: Subject to any disclaimer, the term of this patent is extended or adjusted under 35 U.S.C. 154(b) by 145 days.

(21) Appl. No.: 10/934,802

(22) Filed: Sep. 3, 2004

(65) Prior Publication Data
US 2005/0060198 A1 Mar. 17, 2005

Related U.S. Application Data

(62) Division of application No. 09/611,355, filed on Jul. 6, 2000, now abandoned.

(51) Int. Cl.
*G06F 17/60* (2006.01)
(52) U.S. Cl. .............................. 705/2; 705/3; 600/300; 379/106.02
(58) Field of Classification Search ........... 340/825.52, 340/286.07, 573; 379/106.02, 38; 702/188; 600/300, 509, 513; 235/375, 380; 705/2, 705/3
See application file for complete search history.

(56) References Cited

U.S. PATENT DOCUMENTS

| | | | | |
|---|---|---|---|---|
| 4,237,344 A | * | 12/1980 | Moore | 379/38 |
| 5,974,124 A | * | 10/1999 | Schlueter et al. | 379/106.02 |
| 5,986,568 A | * | 11/1999 | Suzuki et al. | 340/825.52 |
| 6,364,834 B1 | * | 4/2002 | Reuss et al. | 600/300 |
| 6,366,871 B1 | * | 4/2002 | Geva | 702/188 |
| 6,377,162 B1 | * | 4/2002 | Delestienne et al. | 340/286.07 |

FOREIGN PATENT DOCUMENTS

JP 408149216 A1 * 6/1996

OTHER PUBLICATIONS

Manson, Bill "Yes, They Make House Calls S.D. Doctor, Dentist Bring High-Tech Service Home," Los Angeles Times [San Diego County Edition] Apr. 20, 1987. p. 1.*
Registrant: Cybercare, Inc., a Georgia Corporation, Registration/file history Trademark: Electronic Housecall, Reg. No. 2,429,637, registered Feb. 20, 2001, filed Nov. 19, 1999.

* cited by examiner

*Primary Examiner*—C. Luke Gilligan
*Assistant Examiner*—Natalie A. Pass
(74) *Attorney, Agent, or Firm*—Bernard L. Kleinke; Duckor Spradling Metzger & Wynne

(57) ABSTRACT

Mobile clinicians conduct in-home patient visits utilizing on-site diagnostic and treatment equipment, where service is enhanced by the use of portable computing and communications equipment. Initially, a mobile care entity provides a network of predesignated mobile clinicians, each having the use of a preprogrammed portable computer. Each computer is coupled to a wireless communications device, and includes local storage of patient data. Whenever the mobile care entity receives requests for medical service at a patient's premises, the entity selects a mobile clinician and dispatches him/her to the patient's premises. The clinician visits the patient's premises accompanied by an assortment of electronic diagnostic and treatment devices. To examine the patient, the doctor utilizes various diagnostic devices to prepare machine-readable reports of related aspects of the patient's condition.

33 Claims, 7 Drawing Sheets

METHOD FOR CLINICIAN HOUSE CALLS UTILIZING PORTABLE COMPUTING AND COMMUNICATIONS EQUIPMENT

RELATED APPLICATION

This application is a divisional of U.S. patent application Ser. No. 09/611,355, entitled METHOD FOR CLINCIAN HOUSE CALLS UTILIZING PORTABLE COMPUTING AND COMMUNICATIONS EQUIPMENT, filed Jul. 6, 2000, and now abandoned.

BACKGROUND OF THE INVENTION

1. Field of the Invention

The present invention relates to the provision of medical services through clinicians' "house calls." More particularly, the invention concerns a method providing a network of mobile clinicians that individually conduct in-home patient visits utilizing on-site diagnostic and treatment equipment, where service is enhanced by the use of portable computing and communications equipment.

2. Description of the Related Art

With the current American healthcare situation, many sick patients encounter difficulty when attempting to access a physician's office. Some of these difficulties include restrictions on the number or type of health maintenance organization (HMO) visits, limitations of visits to certain preselected physicians, scheduling difficulties, transportation and parking challenges, slow or non-existent insurance reimbursement, and the like. Aged, infirm, or other homebound patients are faced with the particularly difficult challenge of transporting themselves to a physician's office to receive medical attention. Even for ambulatory patients, the current setup can be frustrating to the patient, due to the need to schedule an appointment far in advance.

In contrast to the traditional doctor's office, urgent care centers are geared toward minor, ambulatory emergencies and generally provide office-level care on a walk-in basis. For non-ambulatory patients, the emergency room provides similar barriers to availability as a personal physician's office. Whether ambulatory or not, many patients report a strong aversion to visiting this typically expensive, uncontrolled, slow-moving environment, even among those with a serious medical need. Additionally, gatekeeper triage of acute medical conditions can leave the patient feeling abandoned and the physician feeling that she has taken a measurable risk with the patient's outcome. Nonetheless, there are still more than one hundred thousand visits to American emergency rooms annually. And, even though more than eighty percent of emergency room visits are not necessary to save life and limb, this is sometimes the only alternative for patients requiring prompt service.

As one alternative to visiting an emergency room or a personal physician, some patients call "911" to dispatch an ambulance, especially for medical conditions that are perceived to be particularly serious. Nonetheless, the fanfare and cost of ambulance services can be excessive for many ultimately non-serious medical conditions that typically prompt patients to call an ambulance.

In contrast to the options of meeting a personal physician, visiting an emergency room, or calling an ambulance, many people would prefer to receive acute care in their home or workplace. In fact, the concept of rendering acute care in the home or workplace was the fundamental basis of healthcare for more than four thousand years until the mid-1950s. In the past forty years, however, the concept has fallen out of favor. In fact, between 1960 and 1975, the number of house calls made by family practitioners decreased by seventy-five percent to approximately seventeen million. In 1989, only one million house calls were billed to Medicare. Physicians stopped-making house calls because of many reasons, including inadequate reimbursement, perceived liability, and questions about the quality of care. Each of these concerns is enhanced when dealing with acutely ill patients.

Due to these and other unsolved problems, then, patients' options for obtaining prompt, convenient, acute medical care are not completely adequate today.

SUMMARY OF THE INVENTION

Broadly, the present invention concerns a method of providing medical care, in which mobile clinicians conduct in-home patient visits utilizing on-site diagnostic and treatment equipment, where service is enhanced by the use of portable computing and communications equipment. Initially, a mobile care entity provides a network of predesignated mobile clinicians. The mobile care entity provides each clinician with use of a preprogrammed portable computer, called a "clinician device." Each clinician device is coupled to a wireless communications device and includes local storage of patient data.

According to a predetermined schedule, each clinician device updates patient data in the local storage by utilizing the wireless communications device to download updates from a central storage facility. As an example, this may occur during off-hours on a daily basis, or another appropriate schedule. The mobile care entity receives requests for mobile service to be rendered at a patient's premises. These requests may originate directly from the patient, or from a referral source such as a personal physician, a health care organization, etc. In response to the request for service, the mobile care entity selects one of its predesignated mobile clinicians and dispatches the selected clinician to the patient's premises.

The clinician visits the patient's premises accompanied by an assortment of electronic medical care devices, such as a pulse oximeter, x-ray machine, laboratory analyzer, cardiac output monitoring equipment, etc. The clinician examines the patient, which may include selecting and operating one or more of the on-site medical care devices to analyze one or more aspects of the patient's condition and prepare representative outputs. Beneficially, the clinician device may also interact with off-site diagnostic devices, utilizing a communications interface to access remotely located diagnostic equipment that is unsuitable for transportation to the patient's premises due to size, expense, etc. Then, the clinician directs the clinician device to perform various operations, including (1) electronically collecting the medical care device outputs and presenting them in human-readable form, (2) storing a machine-readable medical record including details of the clinician's examination of the patient, and (3) utilizing the wireless communications device to transmit the machine-readable reports and medical records to the central storage facility.

The foregoing features may be implemented in a number of different forms. For example, the invention may be implemented to provide a method to render on-site medical care. In another embodiment, the invention may be implemented to provide an apparatus, such as a portable computer programmed to assist the on-site clinician as discussed herein. In still another embodiment, the invention may be implemented to provide a signal-bearing medium tangibly embodying a program of machine-readable instructions executable by a digital data processing apparatus to perform operations as discussed herein. Another embodiment concerns logic circuitry having multiple interconnected electrically conductive elements configured to perform operations as discussed herein.

The invention affords its users with a number of distinct advantages. Importantly, the provision of in-home medical services enhances the bond between patient and doctor, as the doctor enters the patient's home and receives the patient's trust. Also, the provision of on-site medical services saves time of busy people, since they can avoid having to drive to the hospital and wait for medical attention and prescription filling. This invention also enables doctors to save money by avoiding the substantial overhead costs of maintaining traditional medical offices. Patients also save money by receiving at-home care rather than hospital commitment, ambulance services, or emergency room visits. This invention is especially useful for elderly or other infirm patients that simply cannot travel to the doctor's office. Also, in non-life threatening cases, the invention helps non-ambulatory patients obtain medical care without the flashing lights, sirens, costs, and other excessive attributes of ambulance service. By providing in-home care, the method of this invention also encourages more rapid discharge of patients after surgery. As another benefit, the invention can be used to provide on-site medical services for sporting events, air shows, beaches, and other public gatherings. The invention also provides a number of other advantages and benefits, which should be apparent from the following description of the invention.

DETAILED DESCRIPTION

Figure 1:
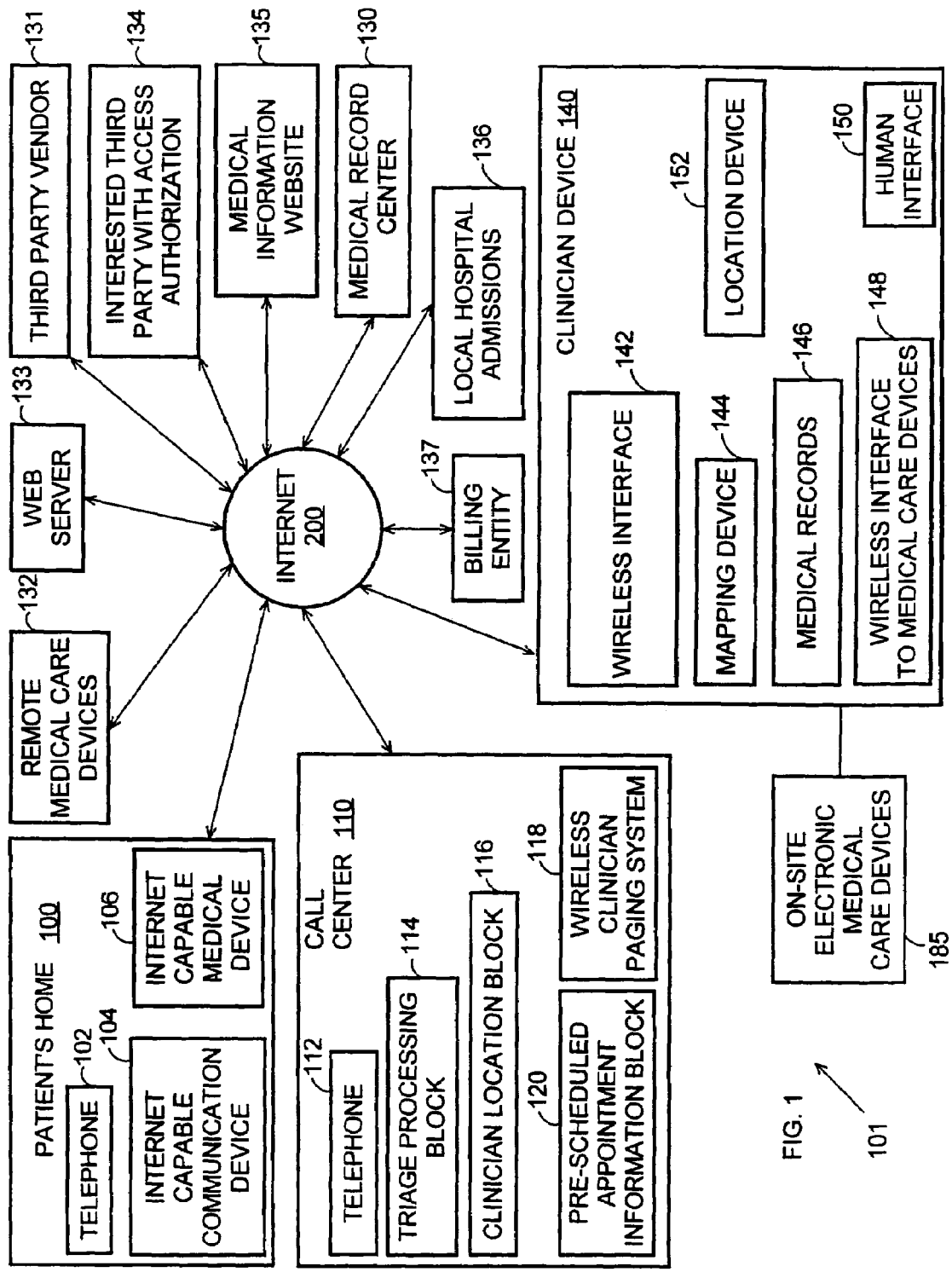
FIG. 1 is a block diagram of the hardware components and interconnections of an in-home medical care environment, according to the invention.

The nature, objectives, and advantages of the invention will become more apparent to those skilled in the art after considering the following detailed description in connection with the accompanying drawings.

HARDWARE COMPONENTS & INTERCONNECTIONS

In-Home Medical Care Environment

One aspect of the invention concerns a system for dispatching medical services, which may be embodied by various hardware components and interconnections. This system is illustrated, along with other related components, utilizing the exemplary operating environment 101 of FIG. 1. The operating environment 101 includes the patient's home 100, a call center 110, clinician device 140, on-site medical care devices 185, the Internet 200, and various secondary components 130–137. Generally, the call center 110 receives and processes requests for in-home medical visits to patients. Medical services are provided at the patient's home 100, which may be equipped with various devices for monitoring and reporting the patient's condition, as shown below. The clinician utilizes the computer-based clinician device 140 to aid in conducting house calls, as explained in greater detail below. As further described below, the secondary components 130–137 include other related components such as remote diagnostic equipment, records storage, third parties, Internet web sites, local hospitals, billing facilities, etc.

In the environment 101, employees or other agents of a "mobile care entity" screen and process incoming calls, dispatch clinicians, store records, process billings, and perform other services related to the providing of on-site medical care. The mobile care entity may comprise a corporation, non-profit group, partnership, sole proprietorship, or other suitable organization.

Patient's Home

Central to the provision of in-home medical services ("house calls") is the patient's home 100, workplace, relative's home (not the patient's), restaurant, mall, sporting event, or any other place where the patient desires to receive medical attention. For ease of reference, this place is referred to as the patient's "home" 100. However, the site 100 is not limited to the patient's living quarters, although this may constitute an illustrative embodiment.

Although the invention contemplates clinicians making self-supported house calls without requiring any equipment at the patient's home 100, the mobile care entity may optionally pre-equip the home 100 with various electronics. For example, the patient's home 100 may be equipped with a telephone 102 for use by the patient in placing calls to the call center 110, and also for use by on-site clinicians. Moreover, the patient's home 100 may also include an internet capable communication device 104, such as a personal computer, web-enabled phone, web-TV, etc. As explained below, the device 104 may serve the patient's requests for medical attention, as well as by on-site clinicians' need to gather information, file reports, etc. The patient's home 100 may also include an internet-capable medical device 106, which comprises one or more machines capable of monitoring the patient's medical condition and transmitting representative reports by the Internet 200, administering medication or other treatment pursuant to remotely transmitted commands, etc. As an example, the device 106 may comprise heart monitoring equipment, dialysis machinery, blood pressure monitoring equipment, respiratory equipment, etc. A custom device programmed to contact the mobile care entity may also be installed at the patient's home 100.

In one embodiment, one or more of the telephone 102, communication device 104, medical device 106 are interconnected to one another other.

Call Center

The mobile care entity operates the call center 110 to receive requests for in-home patient visits. Alternatively, the mobile care entity may hire a subcontractor to perform the services of the call center 110. The call center 110 includes a telephone bank 112, triage processing block 114, clinician location block 116, pre-scheduled appointment information block 120, and wireless clinician paging system 118. In one embodiment, one or more of the telephone 112, triage processing block 114, clinician location block 116, appointment information block 120, and paging system 118 are interconnected to one another.

Depending upon whether the blocks 114–120 are implemented with humans or computers, the telephone bank 112 may be implemented by traditional telephones (used by humans), or automated switching equipment (compatible with computers). The triage processing block 114 includes personnel and/or equipment trained or programmed to receive incoming calls, assess whether the reported medical condition is appropriate for treatment by mobile care entity's clinicians. The mobile care facility may field some conditions appropriate for emergency room treatment, such as influenza, broken bones, non-life threatening abrasions, etc. The triage processing block 114, however, refers life-threatening conditions to more appropriate ambulance, life-flight, or other critical care services.

The clinician location block 116 includes personnel and/ or equipment trained or programmed to identify appropriate clinicians and dispatch them to serve incoming requests. The clinician location block 116 may operate based on geographic proximity, time availability, and other considerations. Once identified, the clinician is paged, called, or otherwise contacted by the wireless clinician paging system 118, which includes personnel and/or equipment that is appropriately trained or programmed for this purpose. As described below, clinicians may be contacted via their clinician devices 140. In one embodiment, the clinician location block 116 receives input from the clinician devices 140 as to the clinician's current geographic location. The clinician location block 116 stores this information for reference at the time of dispatch.

The pre-scheduled appointment information block 120 includes personnel and/or equipment trained or programmed to maintain schedules for the mobile care entity's network of clinicians. Thus, the block 120 may be implemented by scheduling software, physical calendars, or a combination.

Clinician Tools

In addition to operating the call center 110, the mobile care entity hires, contracts, or otherwise maintains a network of mobile clinicians that are available on a full-time, part-time, on-call, or other basis. The mobile care entity provides each clinician with access to a clinician device 140 and a selection of "clinician tools" for on-site patient diagnosis/ treatment, billing, and record keeping. Broadly, the clinician tools include a host of diagnostic and treatment devices, including the on-site medical care devices 185 along with the typical accoutrements of a family physician.

As explained below, each of the medical care devices 185 includes a wireless (as illustrated) or non-wireless communications interface with the clinician device 140. Although the precise details may vary depending upon the application, the devices 185 may include the following items, which may be conveniently stored in a van or other means of transportation: electro cardiograph machine, pulse oximeter, laboratory analyzer, x-ray machine, and the like.

The clinician tools also include other devices without any wireless interface, such as a stethoscope, tongue depressor, thermometers, blood pressure cuff, splints, casts, bandages, sutures, syringes, and other typical equipment of an emergency room, family physician, etc. Furthermore, the clinician may arrive at the patient's house equipped with a mini-pharmacy, constituted by a representative selection of most commonly prescribed drugs. The clinician's tools may further include equipment for performing a broad range of diagnostic procedures and tests, including urinalysis, blood count/chemistry, cholesterol/triglyceride analysis, splinting fractures and broken bones, biopsies, suturing lacerations, constructing casts, pregnancy tests, visual acuity tests, draining abscesses, foreign body removal, pregnancy tests, and the like.

As mentioned above, the clinician also arrives at the patient's home 100 with a portable computer, represented by the clinician device 140. The mobile care entity provides each clinician with access to a clinician device 140. To save costs, clinicians with different working hours may share the same clinician device 140. In one embodiment, each clinician device 140 includes, in one or more housings, a wireless interface 142, mapping device 144, medical records 146, wireless interface 148 for diagnostic equipment, human interface 150, and location device 152, although other embodiments may omit one or more of these. In one embodiment, one or more of these components are interconnected with one another.

In one embodiment, the wireless interface 142 comprises a digital cellular telephone capable of accessing the public Internet 200. As an alternative or additional feature, the interface 142 also include a system to receive pages and/or wireless telephone calls, such as paging messages from the wireless clinician paging system 118. The location device 152 comprises self-locating device such as a global positioning system (GPS) engine, long range navigation (LO-RAN) module, OmniTRACS system, radio frequency receiver, inertial navigation system, etc. The locating device 152 cooperates with mapping device 144 hardware and software to display maps to assist the clinician in reaching the patient's home 100. Although the mapping device 144 may include mapping software, the clinician device 140 may utilize the interface. 142 to access mapping software available through the Internet 200 or other remote site. The medical records 146 comprise a medical records database that is frequently synchronized with patient data contained in the medical record center 130. The wireless interface 148 utilizes Bluetooth technology, infrared, RF, spread spectrum, or other wireless interface to conduct data exchange between the clinician device 140 and wireless components of the on-site diagnostic equipment 185.

The clinician device 140 also includes a human interface 150 data entry, which may include a keyboard, digitizing pen, voice interface, mouse, touch-operated input device, a combination of the foregoing, or other appropriate device(s).

Internet & Secondary Components

As mentioned above, the system 101 also includes a number of secondary components 130–137, with a variety of functions. These secondary components 130–137 as well as the patient's home 100, call center 110, and clinician's device 140 are selectively linked by an appropriate network such as the public Internet 200 (as shown), intranet, wide area network, token ring, etc. The selective linking between these components corresponds to the nature of interaction between components, which is described in greater detail below.

The secondary components 130–137 include a medical record center 130, remote medical care devices 132, web server 133, third party vendors 131, interested third party with access authorization 134, medical information web site 135, local hospital admissions 136, and a billing entity 137. Each of these components has a different type and extent of information exchange with other parts of the system 101, as shown below. Additional secondary components may also be incorporated into the environment 101, depending upon the particular needs of the application.

The medical record center 130 comprises a server, workstation, mass storage device, or other appropriate facility to store medical records for patients of the mobile care entity. The medical record center 130 may be co-located with the call center 110, for example. As one example, the medical record center 130 may provide access to stored medical records through an Internet web site utilizing password checks, firewalls, encryption, or other suitable guarantees of patient security. This information, along with any other information to be shared, may be provided by the web server 133. Depending upon the implementation requirements, communications may be expedited by integrating the web server 133 with one or more other components such as the call center 110, medical records center 130, etc.

The remote medical care devices 132 represent diagnostic and/or treatment equipment located remotely from the patient's home. The devices 132 include computer or other electronic communication components for exchanging information with the on-site clinician and the clinician device 140. Despite their remote location from the patient, the devices 132 are therefore available to diagnose/treat the patient. As illustrated, communications between the remote devices 132 and the clinician device 140 is relayed by the Internet 200. The devices 132 may include equipment that is expensive, bulky, movement-sensitive, unique, or otherwise unsuitable for transportation to the patient's home. Some examples include a $T_cO_2$ machine, End Tidal Capnometer, Pulmonary Function Machine, and the like.

The third party vendor 131 represents an entity such as a home health agency, durable medical equipment manufacturer, or health maintenance organization. The vendor 131 may have reason to communicate with the web server 1.33, medical record center 130, clinician (via clinician device 140) or other clinical components for the purpose of fulfilling Health Care Financing Administration billing requirements, communicating medical info to the physician or receiving medical info, for example.

The interested third party with access authorization 134 represents an entity such as a patient's personal care physician, close friend, partner, or relative with a valid reason to access the medical records 130 to monitor the patient's treatment. In the illustrated embodiment, the third party 134 may access the medical records 130 via the Internet 200.

The medical information web site 135 represents various Internet web sites with reference information that is helpful to mobile care clinicians. The clinicians may access these web sites during on-site patient visits, for example using the patient's internet capable communication device 104, or by using the wireless interface 142 feature of the clinician device 140. Clinicians may also access such web sites after patient visits, for the purpose of performing any follow-up research and diagnosis. Although some content may be provided by the mobile care entity through its web server 133, the web sites 135 are chiefly operated by independent content providers supplying reference and other medical information.

The local hospital admissions 136 represents an admissions desk or other similar facility in a hospital. Communications with the admissions 136 may be helpful, for example, to aid the on-site clinician in admitting the patient to a hospital. Furthermore, hospital admissions 136 may have reason to communicate with the medical record center 130, clinician (via clinician device 140), and other clinical components for the purpose of medical records review, discharge planning or coordinating levels of service.

The billing entity 137 represents an entity such as a contracted billing agency, in-house billing staff, automated billing service or software, etc. The entity 137 may have reason to communicate with the clinical and administrative components or the environment 101 for the purpose of generating Health Care Financing Administration compliant bills, reviewing utilization experience or analyzing trends.

Exemplary Digital Data Processing Apparatus

Figure 2:
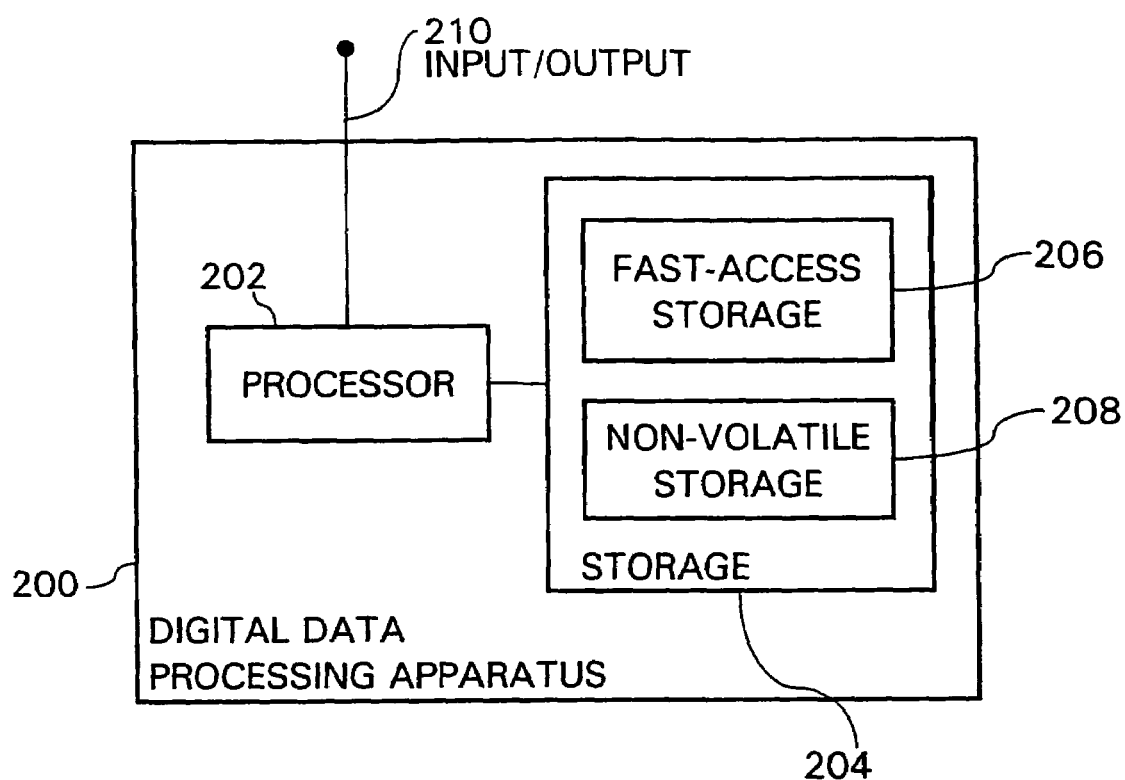
FIG. 2 is a block diagram of a digital data processing machine according to the invention.

Another aspect of the invention concerns a digital data processing apparatus, which may be used to implement the clinician device 140 and other components with data processing functions. This apparatus may be embodied by various hardware components and interconnections; one example is the digital data processing apparatus 200 of FIG. 2. The apparatus 200 includes a processor 202, such as a microprocessor or other processing machine, coupled to a storage. 204. In the present example, the storage 204 includes a fast-access storage 206, as well as nonvolatile storage 208. The fast-access storage 206 may comprise random access memory ("RAM"), and may be used to store the programming instructions executed by the processor 202. The nonvolatile storage 208 may comprise, for example, one or more magnetic data storage disks such as a "hard drive," a tape drive, or any other suitable storage device. The apparatus 200 also includes an input/output 210, such as a line, bus, cable, electromagnetic link, or other means for the processor 202 to exchange data with other hardware external to the apparatus 200.

Despite the specific foregoing description, ordinarily skilled artisans (having the benefit of this disclosure) will recognize that the apparatus discussed above may be implemented in a machine of different construction, without departing from the scope of the invention. As a specific example, one of the components 206, 208 may be eliminated; furthermore, the storage 204 may be provided on-board the processor 202, or even provided externally to the apparatus 200.

Logic Circuitry

In contrast to the digital data storage apparatus discussed previously, a different embodiment of the invention uses logic circuitry instead of computer-executed instructions. Depending upon the particular requirements of the application in the areas of speed, expense, tooling costs, and the like, this logic may be implemented by constructing an application-specific integrated circuit ("ASIC") having thousands of tiny integrated transistors. Such an ASIC may be implemented with CMOS, TTL, VLSI, or another suitable construction. Other alternatives include a digital signal processing chip ("DSP"), discrete circuitry (such as resistors, capacitors, diodes, inductors, and transistors), field programmable gate array ("FPGA"), programmable logic array ("PLA"), and the like.

OPERATION

Having described the structural features of the present invention, the method aspect of the present invention will now be described. Although the present invention has broad applicability to medical care, the specifics of the structure that has been described is best suited for providing a network of mobile clinicians that individually conduct in-home patient visits enhanced by the use of portable computing and communications equipment, and the explanation that follows will emphasize such an application of the invention without any intended limitation.

Signal-Bearing Media

In the context of FIG. 1, such a method may be implemented by operating the clinician device 140, call center 110, medical record center 130, or other components (each as embodied by a digital data processing apparatus 200) to execute respective sequences of machine-readable instructions. In each case, these instructions may reside in various types of signal-bearing media. In this respect, one aspect of the present invention concerns a programmed product, comprising signal-bearing media tangibly embodying a program of machine-readable instructions executable by a digital data processor to perform a method of rendering mobile medical care as described below.

Figure 3:
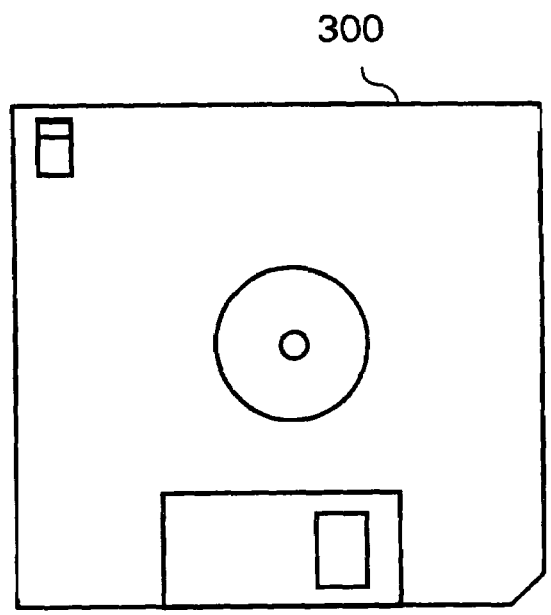
FIG. 3 shows an exemplary signal-bearing medium according to the invention.

As a specific example, this signal-bearing media may comprise, for example, RAM (not shown) contained within the clinician device 140, as represented by the fast-access storage 206. Alternatively, the instructions may be contained in another signal-bearing media, such as a magnetic data storage diskette 300 (FIG. 3), directly or indirectly accessible by the processor 202. Whether contained in the storage 206, diskette 300, or elsewhere, the instructions may be stored on a variety of machine-readable data storage media, such as direct access storage (e.g., a conventional "hard drive," redundant array of inexpensive disks ("RAID"), or another direct access storage device ("DASD")), magnetic tape, electronic read-only memory (e.g., ROM, EPROM, or EEPROM), optical storage (e.g., CD-ROM, WORM, DVD, digital optical tape), paper "punch" cards, or-other suitable signal-bearing media including transmission media such as digital and analog and communication links and wireless. In an illustrative embodiment of the invention, the machine-readable instructions may comprise software object code, compiled from a language such as "C," etc.

Logic Circuitry

In contrast to the signal-bearing medium discussed above, the method aspect of the invention may be implemented using logic circuitry, without using a processor to execute instructions. Logic circuitry may be implemented in the clinician device 140, call center 110, medical record center 130, or other components, where the logic circuitry itself is configured to perform operations to implement the method of the invention. The logic circuitry may be implemented using many different types of circuitry, as discussed above.

Operating Sequences

FIGS. 4–8 provide one illustrative, detailed example of the method aspect of the invention. For ease of explanation, but without any intended limitation, the examples of FIGS. 4–8 are described in the context of the hardware components and interconnections of FIG. 1, as described above.

Mobile Care Setup

Figure 8:
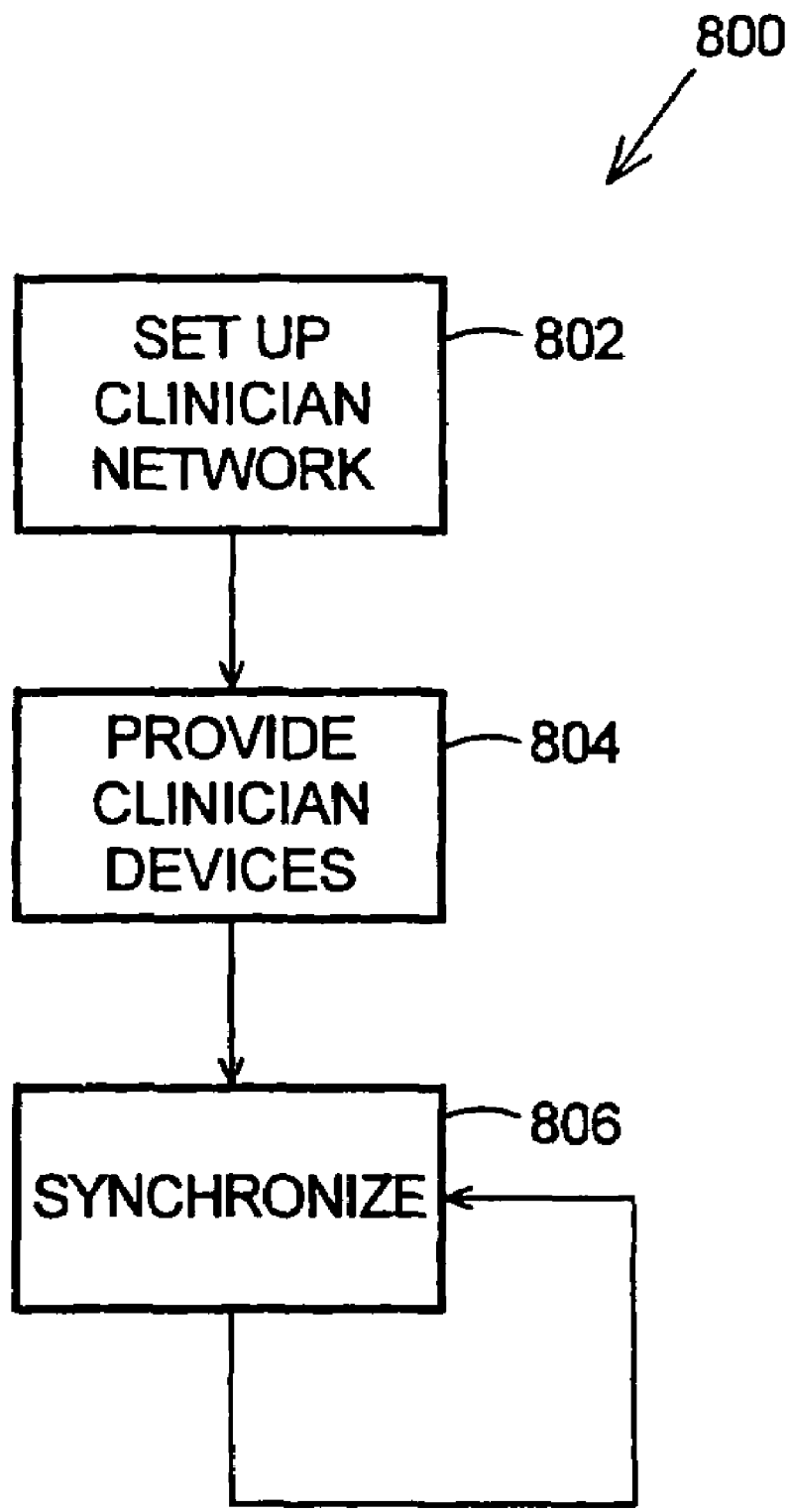
FIG. 8 is a flowchart of a mobile care setup sequence, according to the invention.

FIG. 8 shows a mobile care setup sequence 800, where use and operation of the mobile care environment 100 is initiated. The sequence 800 begins in step 802, where the mobile care entity establishes its network of clinicians. The mobile care entity may construct this network by full-time or part-time hiring of clinicians, enrolling independent contractors, contracting with other agencies, or other suitable relationships. Clinicians may include physicians, specialists such as dermatologist, x-ray technicians, nurses, nurse practitioners, physicians' assistants, paramedics, E.M.T. personnel, or other suitable medical care providers. In step 804, the mobile care entity provides the clinicians with the clinician devices 140, described above. Each clinician has access to at least one of the clinician device 140 while on-duty; clinicians may also have access to clinician devices 140 while on-call if the budget and number of clinician devices 140 permits.

In step 806, clinician devices 140 individually utilize their respective wireless interfaces 142 to self-initiate downloading of patient records from the medical record center 130. To maintain current local records 146, each clinician device 140 automatically repeats the synchronization step 806 whenever an appropriate criteria is met. This criteria may require a periodic, non-periodic, random, or other sufficiently frequent synchronization. The clinician devices 140 may be programmed to synchronize at the same or different times. Synchronization helps the clinician devices 140 preserve the currency of their medical records 146. However, if the number and size of medical records does not permit downloading of all data from the medical records center 130, the synchronization 806 may be limited to certain patients (such as those scheduled for future visits by clinicians associated to the particular device 140), medical records of prescribed recency/type, etc. As an alternative, the timing and extent of each clinician device's synchronization may be manually controlled by a clinician.

Patient Call Initiation

Figure 4:
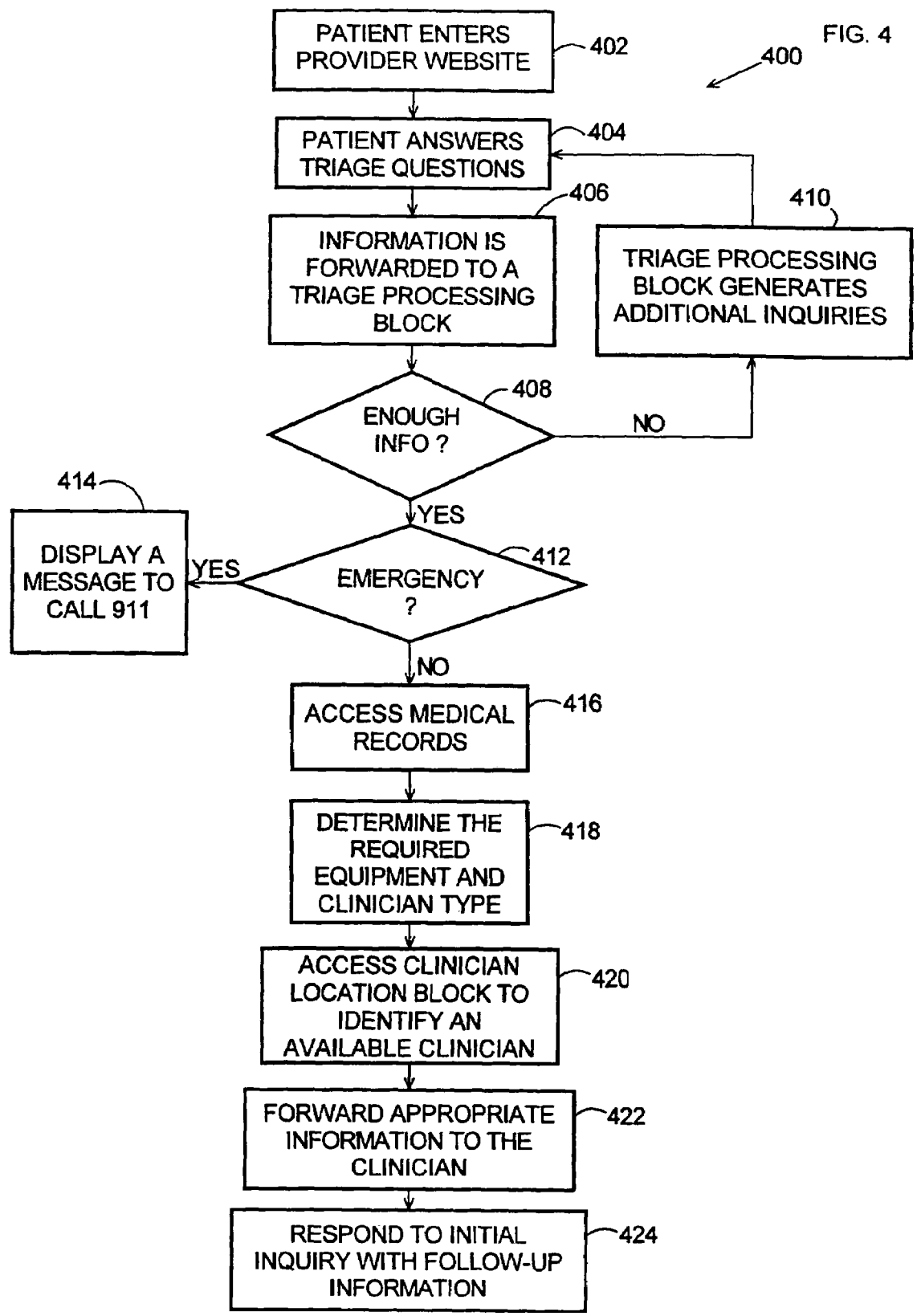
FIG. 4 is a flowchart of a patient call initiation sequence, according to the invention.

FIG. 4 shows a patient call initiation sequence 400. In the sequence 400, a patient requests medical attention from the mobile care entity, and the call center 110 responds by selecting and dispatching a clinician from its network. The sequence 400 begins in step 402, where the patient enters the mobile care facility's web site (supported by the web server 133). In this example, the patient initiates step 402 by using the internet capable communication device 104. As an alternative, the patient may initiate the sequence 400 manually by using the telephone 102 to contact a call center telephone 112, in which case the call processing and triage operations are performed manually by staff (not shown) at the call center 110. For ease of explanation, the following description is limited to the embodiment where automated equipment at the call center 110 processes the patient's call.

Upon receiving initial access by the patient in step 402, the web server 133 queries the patient for name, password, or other indicia that identifies the patient as an existing customer of the mobile care entity. Having identified the patient, the web server 133 proceeds to gather information from the patient as to his/her medical condition (step 404). Namely, the patient answers certain predetermined "triage" or "screening" questions, which may include a series of interactive inquiries based upon the appropriate triage algorithm. In one embodiment, the patient answers these inquiries by mouse-clicking on alternative choices, entering typed text, etc.

Next, the web server 133 forwards the patient's triage answers to the triage processing block 114 (step 406), which determines whether there is enough information to process the patient's call (step 408). If not, the triage processing block generates additional inquiries (step 410) and returns to step 404. When the triage processing block 114 determines that the patient has provided sufficient information to proceed (step 408), the triage processing block 114 determines whether the patient's condition presents a life-threatening situation (step 412). In one embodiment, the triage processing block accesses medical information stored locally or via Internet 200 in order to determine the outcome of the triage process. If the patient's condition constitutes a life-threatening situation, the triage processing block 114 directs the web server 113 to display a message instructing the patient to obtain emergency ambulance services, for example by dialing "911" (step 414). Thus, the call center 110 refuses the patient's call, since it is more appropriate for ambulance or other rapid deployment services rather than an on-site clinician visit.

If the patient's situation is not an emergency, step 412 leads to step 416, where the triage processing block 114 retrieves the patient's medical records. The medical records may be retrieved from a third party vendor 131 (such as the patient's primary care physician), from the medical record center 130, locally from the call center 110, or another source. Moreover, the records may be retrieved by hand, over the Internet 200, by facsimile machine, or other automated or manual means.

Next, in step 418 the triage processing block determines the appropriate clinician type and equipment required to treat the patient's reported condition. As mentioned previously, clinicians may have qualifications of various levels, such as nurses, nurse practitioners, physicians, x-ray technicians, and the like. In one exemplary case, an appropriate clinician/device may be a nurse qualified to take blood (clinician) and a blood analyzer (device). In a different case, an appropriate clinician/device may be a physician (clinician) accompanied by an x-ray technician (second clinician) and x-ray machine (device). Some examples of other clinician/device combinations include cardiologist, and impedance monitor, ultrasound machine and technologist, and other specialists. As one example, step 418 may be performed by utilizing a software module such as an expert system.

After the triage processing block 114 identifies the appropriate type of clinician for the current patient (step 418), the clinician location block 116 identifies (step 420) and thereby selects a clinician in the mobile care entity's network to satisfy the requirements of clinician type from step 418. This may be performed by consulting a look-up table or other cross-referencing guide, for example. Some exemplary considerations for step 420 include (1) the urgency of the patient's request, (2) the geographical location of both patient and candidate clinician, (3) the clinician's status as being on-duty busy, on-duty idle, on-call, off-duty but available, (4) the clinician's pre-scheduled appointments available from the pre-scheduled appointment information block 120, etc. Step 420 may select multiple clinicians if required, such as an x-ray technician visit at one o'clock and then a physician follow-up visit at two o'clock.

The wireless clinician paging system 118 then transmits a dispatch notification to the selected clinician, including forwarding of sufficient information to the clinician to initiate the house call (step 422). This information identifies the patient's name, the patient's address and telephone number, the reported medical condition, and other information needed to initiate the house call. Further information may include, for example, call center instructions resulting from patient triage/interview, information on the patient's reported condition, call priority, proposed or promised arrival time, etc. This information may be conveyed to the clinician by various means, such as (1) the call center 110 transmitting a message to the Internet 200 for subsequent retrieval by the clinician, wireless internet connection, (2) standard cellular telephone or paging system, (3) standard wireless paging system, (4) proprietary wireless system such as NEXTEL, or (5) other suitable means. The on-call clinician receives this information at his/her clinician device 140, via the wireless interface 142.

In step 424, the triage processing block 114 responds to the patient's initial call (from step 402) by providing the patient with certain follow-up information, such as the name of any clinicians that have been dispatched, proposed arrival time, etc. The block 114 may convey this information to the patient by telephone 102, e-mail, updating a confidential patient status area on the web site 133, etc. Furthermore, the triage processing block 114 may transmit e-mail or other suitable messages to other interested parties, or make such information available to parties with access authorization 134. Such parties may include, for example, the patient's primary care physician, pre-registered friends/relatives, those with e-mail addresses entered by the patient during initial registration with the mobile care entity, insurance providers, etc. This completes the sequence 400.

Automatic Call Initiation

Figure 5:
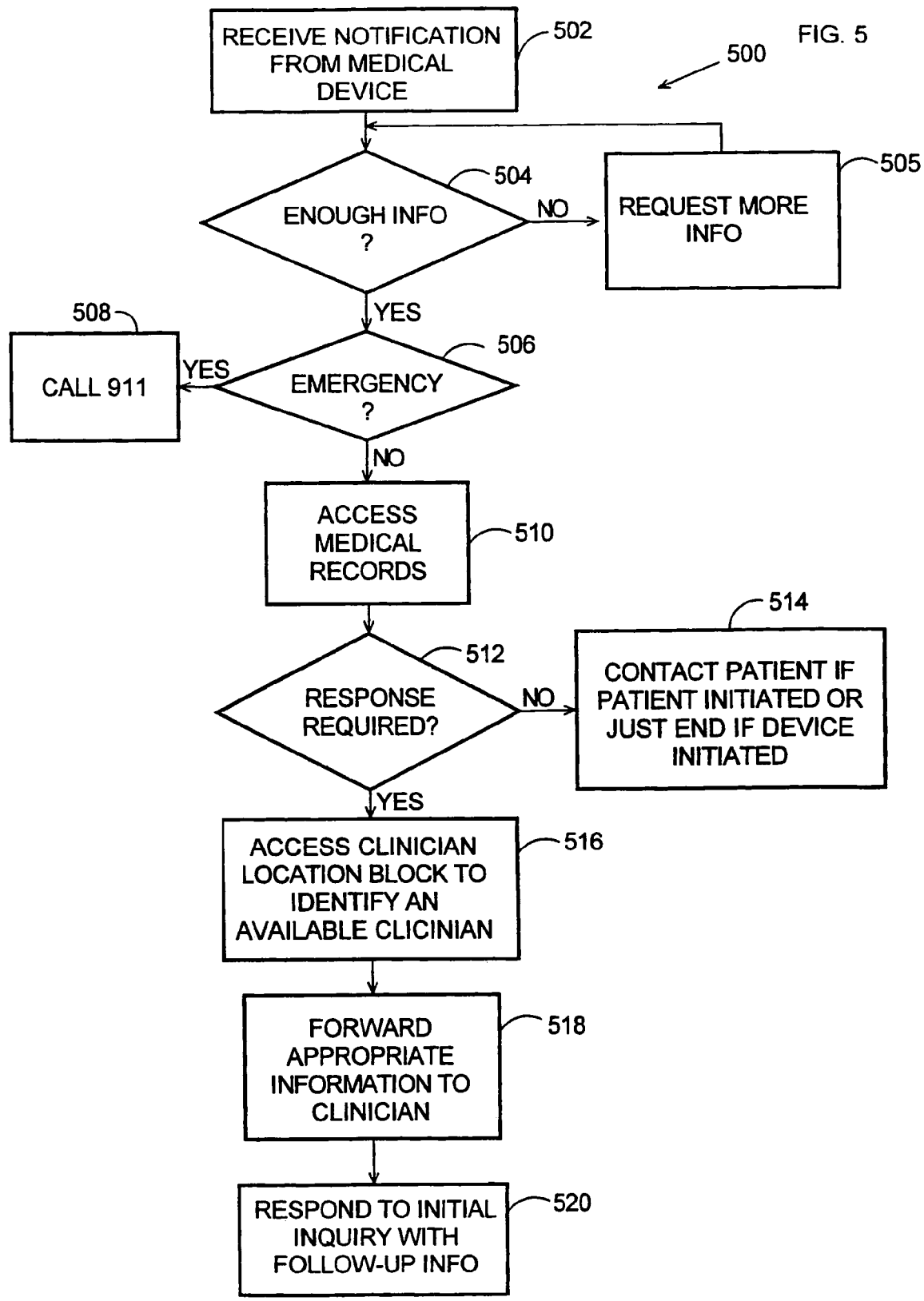
FIG. 5 is a flowchart of an automatic call initiation sequence, according to the invention.

FIG. 5 shows an automatic call initiation sequence 500. In the sequence 500, automatic equipment installed at the patient's home requests medical attention from the mobile care entity, and the call center 110 responds by selecting and dispatching one or more clinicians from its network. The steps are initiated in step 502, where the internet capable medical device 106 transmits notification to the triage processing block 114. This notification can take various forms, such as a periodic report, an emergency request automatically generated in response to a condition such as dangerously low blood pressure, manually generated emergency request such as the patient's manual activation of a "panic button," etc.

In response to the notification of step 502, the triage processing block 114 determines whether the notification contains sufficient information to begin the process of dispatching a clinician (step 504). If not, the call center 110 initiates a request for additional information (step 505). In one example, this request may occur manually, by call center staff placing a telephone call to the patient. In another example, the triage processing block 114 may submit a machine-initiated request for additional information, for example by querying the medical device 106.

When there is sufficient information to process the notification of step 502, the triage processing block 114 determines whether the patient's situation constitutes a life-threatening emergency. If so, the call center 110 directs the patient to obtain emergency medical care (step 508), for example by dialing "911." If the notification of step 502 arose from the patient activating a panic button, step 508 may be satisfied by call center 110 staff contacting the patient by telephone 102 or calling an ambulance on behalf of the patient. On the other hand, if the notification of step 502 arose from the medical device 106, step 508 may involve the triage processing block 114 returning an automated message to the medical device 106 or calling an ambulance on behalf of the patient.

If the present situation does not constitute an emergency, the triage processing block 114 retrieves the patient's medical record (step 510). The medical records may be retrieved from a third party vendor 131 (such as the patient's primary care physician), from the medical record center 130, locally from the call center 110, or another source. Moreover, the records may be retrieved by hand, over the Internet, by facsimile machine, or other automated or manual means.

Next, in step 512 the triage processing block 114 determines whether any response by an on-site clinician is required. This step is performed by evaluating the notification (from step 502), any additional information (from step 505), and the patient's medical record (from step 510). The evaluation of step 512 may be performed, for example, by using an expert system software module, or performing pre-programmed comparison with a list of various conditions for which clinician dispatch is required. If clinician dispatch is not needed, the patient is contacted and advised accordingly. Namely, call center 110 staff may manually contact the patient, or the triage processing block 114 may automatically contact the patient by sending an appropriate message to the medical device 106 and/or the device 104.

On the other hand, if step 512 mandates clinician dispatch, the triage processing block 114 proceeds with step 516. Particularly, the block 114 determines the appropriate clinician type and equipment required to treat the patient's reported condition, and then the clinician location block 116 identifies and thereby selects an on-call clinician in the mobile care entity's network to satisfy these requirements. The wireless clinician paging system 118 then transmits a dispatch notification to the selected clinician, including forwarding of sufficient information to the clinician to initiate the house call (step 518).

In step 520, the triage processing block 114 responds to the original notification of step 502 by providing the patient with certain follow-up information, such as the name of any clinician(s) scheduled to visit the patient and the proposed arrival time(s). This completes the sequence 500.

Clinician Notification

Figure 6:
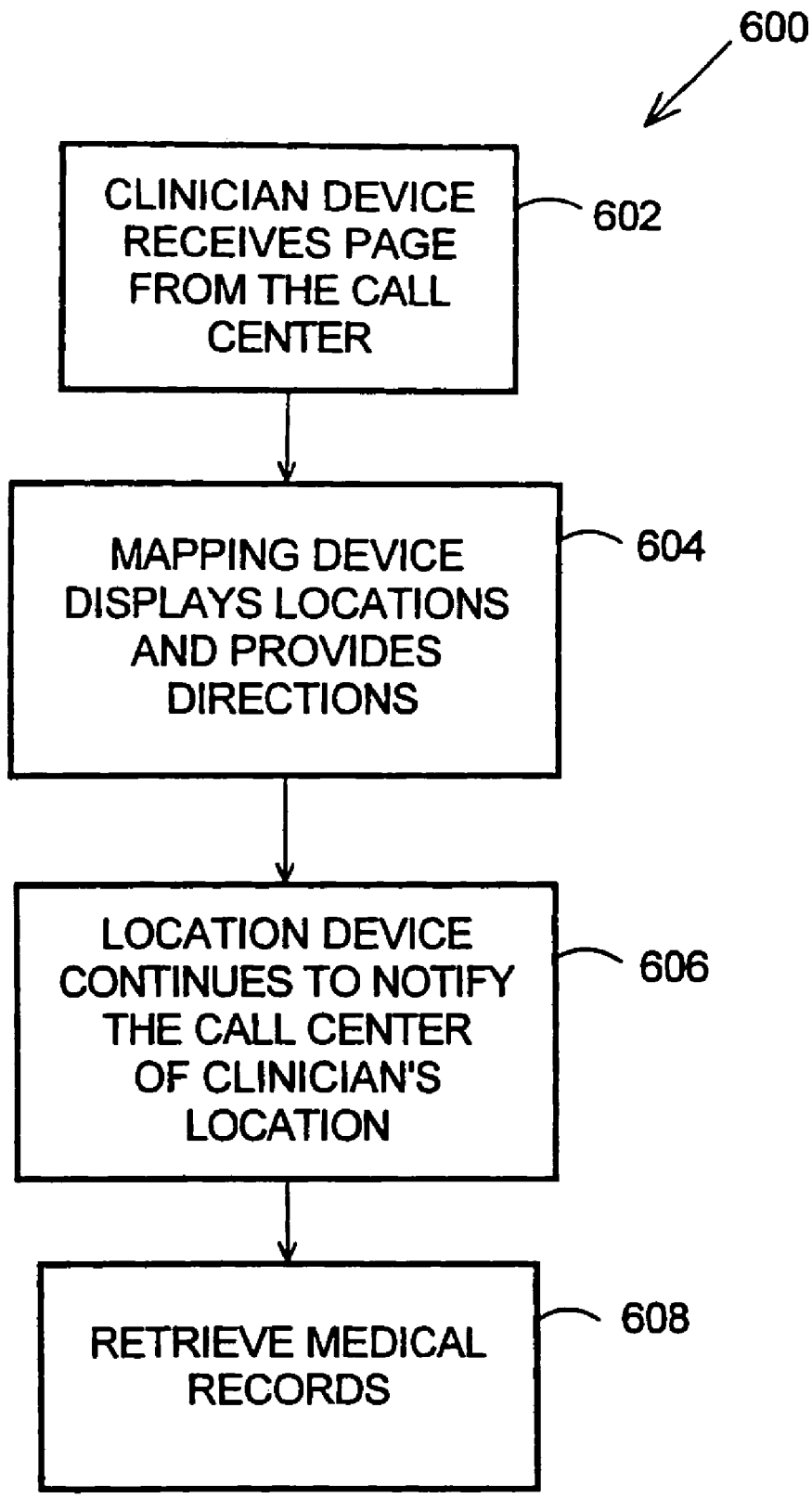
FIG. 6 is a flowchart of a clinician notification sequence, according to the invention.

FIG. 6 shows a clinician notification sequence 600, where the clinician receives dispatch notification from the call center 110 and responds accordingly. The steps are initiated in step 602, when the clinician device 140 receives the call center's dispatch notification (transmitted previously in steps 422 or 518, as discussed above). As mentioned above, this information identifies the patient, the reported medical condition, and other information needed to initiate the house call, and may include further information such as diagnosis/treatment instructions or allergy alerts resulting from patient triage/interview, information on the patient's reported condition, call priority, proposed arrival time, etc.

In response to the dispatch notification from step 602, the mapping device 144 component of the clinician device 142 consults the location device. 152 to determine the clinician's current location (step 604). Also in step 604, the mapping device 144 prepares a map including the clinician's present location (from the device 152), the patient's location (from the call center's dispatch notification), and appropriate driving directions between these sites.

Next, in step 606 the clinician device 140 transmits a message reporting the location of the clinician device 140. To aid the call center 110 in monitoring the clinician's progress toward the patient's home, location reporting messages may be repeatedly transmitted to the call center 110 in response to: (1) occurrence of a repeating time period, such as one minute, (2) call center queries, (3) significant changes in clinician location, or (4) another reason.

After step 606, the clinician device 140 retrieves the patient's medical records. This is performed by operating the interface 142 to contact the medical record center 130 via the Internet 200, and retrieving the patient's most updated medical records. Also, the clinician device 140 updates any locally stored medical records 146 with the current information from the medical record center 130. Alternatively, rather than actively obtaining the patient's medical records, the clinician device 140 may receive unsolicited transmission of the patient's medical records by the call center 110. After step 608, the sequence 600 is complete and the clinician is ready to render on-site patient care upon arrival.

On-Site Patient Diagnosis/Treatment

Figure 7:
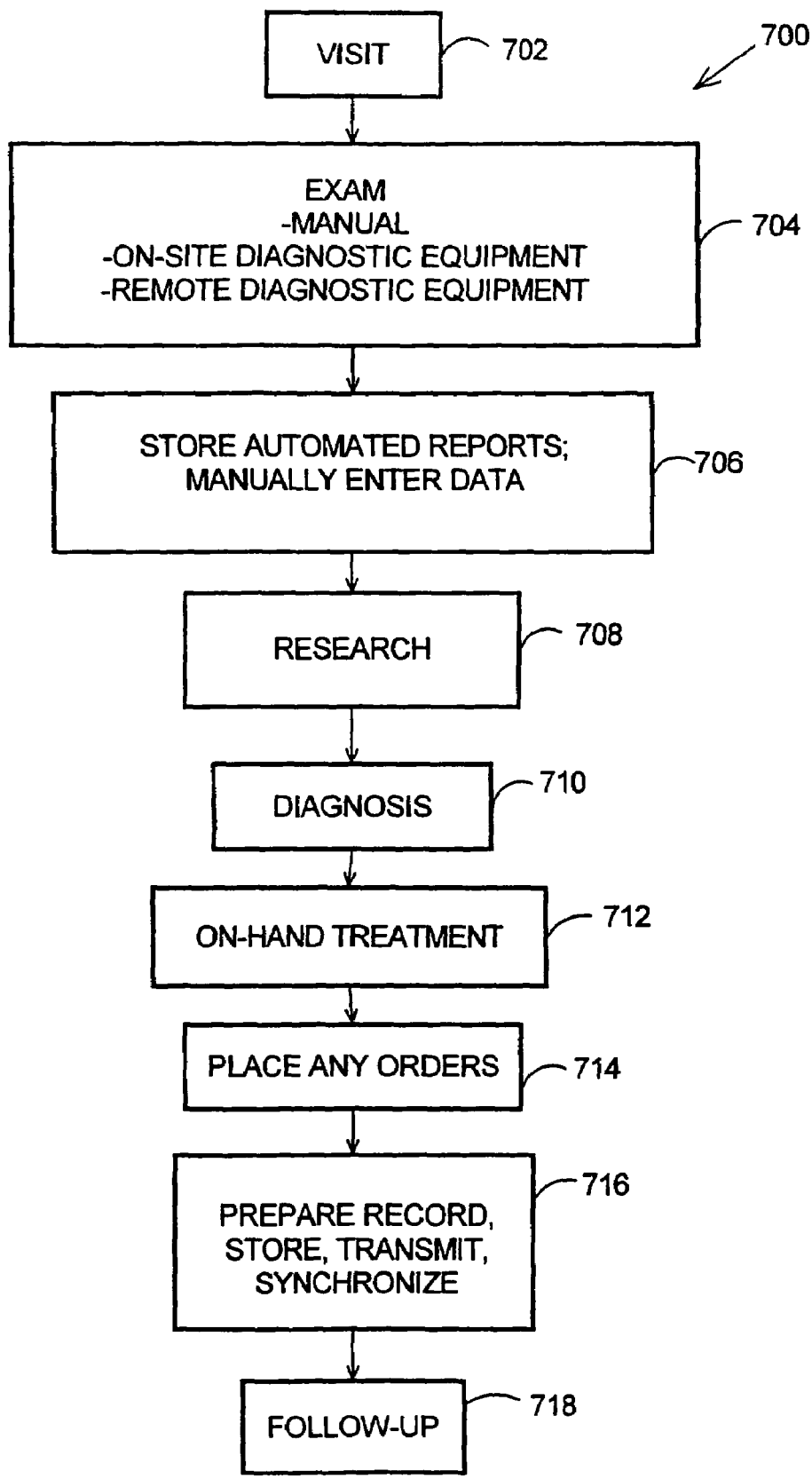
FIG. 7 is a flowchart of an on-site patient diagnosis/treatment sequence, according to the invention.

FIG. 7 shows the sequence for on-site patient diagnosis/treatment, as performed by the clinician. The sequence 700 begins in step 702, when the clinician visits the patient's home 100 after having been dispatched as discussed above. The clinician is accompanied by the clinician device 140, on-site electronic medical care devices 185, and other clinician tools as discussed above.

In step 704, the clinician examines the patient. The clinician selects and operates various of the clinician's tools to conduct the examination. With traditional, manually-operated tools such as thermometers, blood pressure cuffs, and the like, use and feedback occurs in traditional fashion. The clinician may enter data from such manual examination into the clinician device 140 for inclusion into the patient's medical record and/or analysis by diagnostic programs of the clinician device 140.

In contrast to traditional examination means, the clinician may perform more automated examination by coupling appropriate sensors between one or more on-site electronic medical care devices 185 (such as a laboratory analyzer) and the patient's proximity, body, bodily fluids, or tissue, whereupon the device(s) 185 analyze the bodily component under scrutiny and provide a representative output. In one case, the output may comprise a human-readable output medical care devices 185 present directly to the clinician. In other cases, the output of one or more of the devices 185 may comprise a machine-readable output presented to the clinician device 140; in this embodiment, the clinician device 140 and device 185 communicate by the wireless link 148, although other means may be used as well such as infrared link, cables, fiber optic lines, etc. If the output of the device 185 is machine-readable, then the clinician device 140 collects this output and responsively provides a table, graph, diagram, or other human-readable presentation by computer display, printing, etc.

In addition to using on-site clinician tools, the clinician may also employ one or more remotely located medical care devices 132. For this purpose, the clinician couples sensors between the clinician device 140 and the patient's proximity, body, bodily fluids, or tissue. The sensors measure various physiological conditions and relay representative information in machine-readable form to the clinician device 140. In turn, the clinician device 140 invokes the wireless interface 142 to further relay these measurements to the remote device(s) 132, retrieve any resultant analysis from the remote devices, and locally present the results for the clinician in human-readable form.

In step 706, the clinician manually enters data from the patient's examination, and also utilizes the clinician device 140 to store the output of the devices 185/132, whether such output occurs in human or machine-readable form. Furthermore, the clinician may direct the clinician device 140 to store any human-readable reports that it has prepared utilizing machine-readable output of the devices 185. If desired, the clinician may direct the clinician device 140 to transmit results from the diagnosis (including output from devices 185) to the call center 110 for immediate evaluation by another clinician, for inclusion in the patient's medical record by call center personnel, etc.

As shown in step 708, the clinician may supplement his/her evaluation of the patient's condition by utilizing the clinician device 140 and wireless interface 142 to access various medical information web sites 135 or other sources of information about drug interactions, symptoms, treatment strategies, etc. After step 708, the clinician then diagnoses the patient (step 710) and renders any on-site treatment (step 712), if possible. The clinician may immediately prescribe and render medicine that s/he has brought along, as well as dispatch any available medical products, such as slings, casts, sutures, bandages, etc. As for medicine or products that are not immediately available, the clinician may choose to order them (step 714) from a third party vendor 131. Advantageously, the order may be placed in immediately using the clinician device to contact the third party vendor 131 via the Internet 200. Such products may include walkers, special beds, oxygen, leased medical equipment, and the like.

Next, in step 716, the clinician prepares a record of the at-home patient visit by assembling the clinician's notes, reports from the clinician device 140, output from the equipment 185/132, and the like. The clinician stores a machine-readable representation of this record, for example in the medical records 146. At this time, or later, the clinician invokes the wireless interface 142 to transmit the machine-readable representation of the patient's report to the medical record center 130.

Having completed the patient's visit, the clinician then performs various follow-up steps 718. For instance, on behalf of the patient, the clinician may utilize the clinician device 140 to complete an on-line admission process to a local hospital 136 if the patient's condition warrants. The clinician may also schedule one or more follow-up visits by manually contacting call center personnel, or by utilizing the clinician device 140 and wireless interface 142 to notify the pre-scheduled appointment information block 120 with follow-up information. In addition, the clinician device 140 may transmit an e-mail message to a friend, relative, personal care physician, or other pre-identified party after completion of the clinician's at-home visit. This e-mail message, which may be transmitted automatically by the clinician device 140 or manually by the clinician, contains information reporting the patient's examination, diagnosis, and treatment. At this time, the clinician may also receive, review, and respond to any e-mail messages that have been forwarded by the call center 110 from any interested third parties 134. Other possible follow-up action includes various billing matters, such as transmitting messages to invoke the billing entity 137, sending completed Health Care Financing Administration records to a referring home health agency, etc. Moreover, such billing operations may be performed automatically at the completion of the patient's visit, or by the clinician's use of the clinician device. Finally, the clinician utilizes the clinician device 140 to notify the call center 110 that the visit is complete.

OTHER EMBODIMENTS

While the foregoing disclosure shows a number of illustrative embodiments of the invention, it will be apparent to those skilled in the art that various changes and modifications can be made herein without departing from the scope of the invention as defined by the appended claims. Furthermore, although elements of the invention may be described or claimed in the singular, the plural is contemplated unless limitation to the singular is explicitly stated. Additionally, ordinarily skilled artisans will recognize that operational sequences must be set forth in some specific order for the purpose of explanation and claiming, but the present invention contemplates various changes beyond such specific order.

What is claimed is:

1. A method of providing medical treatment by licensed physicians, comprising operations of:

a mobile care entity providing a network of predesignated mobile licensed physicians;

the mobile care entity providing the licensed physicians with use of preprogrammed portable computers, each portable computer coupled to a wireless communications interface and including local storage of patient medical records;

determining a current location of the licensed physicians using GPS self-locating devices located with each of the licensed physicians;

receiving at the mobile care entity the current locations of the licensed physicians;

storing patient medical records at a central storage facility;

according to a predetermined schedule, transmitting wirelessly current medical records from a central storage facility to the local storage in each portable computer for automatically updating patient medical records in the local storage by utilizing the wireless communications interface;

the mobile care entity receiving a request for medical services from a patient at the patient's premises;

the mobile care entity selecting one of the predesignated mobile licensed physicians in view of the requested medical services and the current locations of the licensed physicians;

the mobile care entity dispatching the selected licensed physician to the patient's premises by sending a notification signal to the selected licensed physician using a wireless medical care provider electronic paging system;

the selected licensed physician visiting the patient's premises accompanied by the portable computer and a preselected collection of portable electronic medical care devices, at least one of the portable electronic medical care devices including a wireless device communications interface with the portable computer of the selected licensed physician;

the selected licensed physician examining the patient at the patient's premises, including selecting and operating one or more of the portable electronic medical care devices to analyze one or more aspects of the patient's condition and prepare representative outputs for transmission wirelessly to the portable computer in response to the notification signal;

storing the outputs in the local storage of the portable computer of the selected licensed physician;

the selected licensed physician updating the patient's medical record stored in the local storage at the patient's premises; and the selected licensed physician directing the portable computer to perform follow-up operations including:

electronically collecting the outputs of the portable electronic medical care devices utilizing the wireless device communications interfaces directly to the portable computer and presenting them in human-readable form;

wirelessly transmitting from the portable computer the outputs of at least one of the portable electronic medical care devices stored in the local storage directly to at least one remote medical care device including remote treatment equipment for analyzing the outputs of the portable electronic medical care devices for the patient;

analyzing the transmitted outputs of the portable computer by the remote treatment equipment;

wirelessly retrieving with the portable computer said analysis of the outputs directly from the remote treatment equipment;

storing the retrieved analysis from the remote treatment equipment in the local storage of the portable computer;

displaying on the portable computer to the selected licensed physician in the patient's premises a portion of the patient's medical records, the outputs of the portable electronic medical care devices, and said analysis from the remote treatment equipment;

treating the patient at the patient's premise by the selected licensed physician in response to the information displayed on the portable computer;

inputting orders at the patient's premises by the selected licensed physician into the portable computer for the care of the patient;

wirelessly sending at least one of the orders from the patient's premises at the time of treating the patient by the selected licensed physician to at least one third party vendor via the portable computer for products or services to be provided by the third party vendor;

updating in the local storage the patient's medical record with the observations from the selected licensed physician's examination of the patient, and the retrieved analysis from the remote medical care device of the patient at the patient's premises at the time of treating the patient;

storing the updated patients medical record in the local storage; and utilizing the wireless communications interface to transmit the updated medical record of the patient from the local storage to the central storage facility for storage therein to synchronize the medical records.

2. The method of claim 1, the medical care devices including at least one of the following:
an x-ray machine;
a cardiac output monitoring machine;
laboratory analyzer;
a pulse oximeter.

3. The method of claim 1, the operations further comprising:
the selected licensed physician treating the patient; and
the selected licensed physician directing the portable computer to store a machine-readable record including a summary of the selected licensed physician's treatment of the patient.

4. The method of claim 1, the wireless communications interface comprising a mobile digital telephone.

5. The method of claim 1, the wireless communications interface comprising a radio frequency transceiver.

6. The method of claim 1, the selected licensed physician further directing the portable computer to perform operations comprising:
directing the portable computer and wireless communications interface to transmit selected machine-readable reports and records from the local storage to a patient referral source.

7. The method of claim 1, the operations further comprising:
each portable computer tracking and recording various event times related to the patient visit, including at least one of the following: dispatch time, travel time, patient visit time.

8. The method of claim 1, the downloading of updates from the central storage facility being performed, via the public Internet.

9. The method of claim 1, the operation of utilizing the wireless communications interface to transmit the machine-readable record to the central storage facility comprising:
transmitting the record to the central storage facility via the public Internet.

10. The method of claim 1, the operation of the selected licensed physician examining the patient further comprising:
the selected licensed physician interconnecting one or more sensors between the patient and the portable computer;
the selected licensed physician directing the portable computer to gather machine-readable representations of bodily conditions measured by the sensors, and transmit the representations via the wireless communications interface to a remotely located electronic medical care device; and
the portable computer communicating with the remotely located device to obtain a machine-readable output representing analysis performed by the remotely located device.

11. The method of claim 10, the operation of obtaining, a machine-readable output representing analysis performed by the remotely located device further comprising:
the portable computer presenting the results in human-readable form to the selected licensed physician.

12. The method of claim 1, the operation of the selected licensed physician examining the patient further comprising:
the selected licensed physician directing the portable computer and communications interface to cooperatively engage in machine-readable communications with a remotely located electronic medical care device to report bodily conditions of the patient to the remotely located device and receive analysis based thereon.

13. The method of claim 12, the remotely located electronic medical care device including an ultrasound machine.

14. The method of claim 1, the operations further comprising:
the selected licensed physician directing the portable computer and communications interface to obtain information provided by Internet web sites.

15. The method of claim 1, the operations further comprising:
while at the patients premises, the selected licensed physician utilizing the portable computer to place orders for medical supplies over the Internet.

16. The method of claim 1, the operations further comprising:
the operation of receiving a request for medical services at a patients premises comprising the mobile care entity receiving patient medical information transmitted by a medical device located at the patient's premises.

17. The method of claim 1, the dispatching of the selected licensed physician to the patients premises including sending wireless dispatch information to the selected licensed physician, including patient medical record information, current medical condition information, and patient location information.

18. The method of claim 1, the operations further comprising:
responsive to the request for medical services, transmitting a machine-readable notification of the request to a pre-registered party.

19. The method of claim 1, the operations further comprising:
responsive to the request for medical services, transmitting a machine-readable response to the patient including at least one of the following: posting a message upon an Internet web site, transmitting an e-mail message.

20. The method of claim 1, the operations further comprising:
responsive to the request for medical services, transmitting a machine-readable notification of at least one of the following to the patient: geographic location of the selected licensed physician, and expected arrival time of the selected licensed physician at the patient's premises.

21. The method of claim 1, the operations further comprising:
responsive to completion of the selected licensed physician's visit to the patient, conducting automatic computer-driven operations including generating and transmitting an e-mail notification to a pre-registered pasty.

22. The method of claim 1, the operations further comprising:
responsive to completion of the selected licensed physician's visit to the patient, conducting automatic computer-driven operations including:
scheduling of a follow-up visit; and
transmitting machine-readable notification of the scheduled follow-up visit to a pre-registered party.

23. The method of claim 1, the operations further comprising:
automated medical-condition monitoring equipment at the patient's premises generating and transmitting the request for medical services to the mobile care entity.

24. The method of claim 1, the follow-up operations further comprising:
the selected licensed physician operating the portable computer to prepare and make wireless transmission of one or more orders for items related to the examination for delivery to the patient.

25. The method of claim 1, the follow-up operations further comprising:
the selected licensed physician operating the portable computer to prepare and make wireless transmission of information to admit the patient to a hospital.

26. A method of patient treatment comprising:
according to a predetermined schedule, transmitting wirelessly current medical records from a central storage facility to local storage in a portable computer for automatically updating patient medical records in the local storage by utilizing a wireless communication interface:
receiving in the local storage of the portable computer a wireless dispatch notification including dispatch information concerning a patient including current patient location information, and current medical symptoms;
determining present position of the portable computer utilizing a GPS self-locating device;
utilizing the present position and the patient location information to generate directions to the patient;
visiting the patient accompanied by the portable computer having the wireless communication interface and a preselected collection of portable electronic medical care devices, at least one of the devices including a wireless device communications interface with the portable computer;
examining the patient with one or more of the portable electronic medical care devices providing outputs to the portable computer via the wireless device communications interface by applying at least one of the portable electronic medical care devices to the patient in response to the dispatch notification;
wirelessly transmitting the outputs of at least one of the portable electronic
medical care devices to the portable computer;
storing the outputs in the local storage of the portable computer at the patient's location;
wirelessly transmitting the outputs from the local storage of the portable computer at the patient's location directly to at least one remote medical care device for analysis including remote treatment equipment;
analyzing the tramsmitted outputs by the remote treatment equipment;
wirelessly retrieving said analysis directly from the remote treatment equipment via the portable computer at the patient's location;
storing the analysis in the local storage of the portable computer at the patient's location;
displaying on the portable computer at the patient's location a portion of the medical records, the outputs of the portable electronic medical care devices, and the analysis from the remote medical care device;
treating the patient according to the information displayed on the portable computer;
entering medical treatment information including prders for the care of the patient into the portable computer in response to patient treatment at the patient's location;
wirelessly sending at least one of the orders from the patient's location at the time of treating the patient to at least one third party vendor via the selected portable computer for products or services to be provided by the third party vendor;
storing the medical treatment information in the local storage of the portable computer at the patient's location; and
wirelessly transmitting from the local storage of the portable computer at the patient's location said medical treatment information, the outputs of the medical care devices, and the analysis from the remote medical care device to a central storage facility to synchronize the medical records via the portable computer.

27. The method of claim 26, further comprising wirelessly ordering delivery of medication for said patient via the interface of the portable computer.

28. The method of claim 26, further comprising wirelessly ordering delivery of medical equipment for said patient via the interface of the portable computer.

29. The method of claim 26, wherein said medical treatment information comprises a request to automatically schedule a follow-up visit for said patient.

30. The method of claim 26, further comprising wirelessly contacting a predetermined party as to said medical treatment information via e-mail.

31. The method of claim 26, further comprising wirelessly transmitting admission information for admitting said patient to a hospital.

32. The method of claim 26, further comprising sending wireless notification of a current medical care provider location.

33. A method of providing medical treatment by licensed physicians, comprising:

providing a plurality of mobile licensed physicians, with portable computers each being equipped with local storage, and with portable wireless on-site electronic medical care devices for analyzing patient conditions and for transmitting the condition information to the portable computer wirelessly;

determining the location of the mobile licensed physicians;

receiving a dispatch notice for a given patient at a selected portable computer of an appropriate mobile physician depending on the current location of the appropriate licensed physician in response to a request for medical care at the given patient's premises;

prior to arrival of the appropriate mobile physician at the given patient's premises, wirelessly downloading to the selected portable computer from a remote central storage facility a complete medical record for the given patient to enable the mobile physician to treat the given patient;

prior to arrival of the appropriate mobile physician at the given patient's premises, storing the downloaded complete medical record in the local storage in the selected portable computer of the appropriate mobile physician;

transporting the selected portable computer storing the complete medical record and the wireless on-site medical care devices to the given patient's premises by the appropriate mobile physician:

applying by the appropriate mobile physician at least one of the wireless on-site medical care devices to the given patient in the given patients premises in response to the dispatch notice;

wirelessly sending patient information from the on-site medical care devices directly to the selected portable computer at the given patient's premises;

storing the patient information in the local storage of the selected portable computer;

directly communicating wirelessly between the selected portable computer at the given patient's premises and at least one remote medical care device including remote treatment equipment for analyzing the patient information for the given patient;

analyzing the patient information for the given patient by the at least one remote treatment equipment;

wirelessly receiving in the selected portable computer at the given patient's premises said analysis from the remote treatment equipment;

storing the analysis received from the remote treatment equipment in the local storage of the selected portable computer;

displaying on the selected portable computer to the appropriate mobile physician in the given patient's premises a portion of medical record, said patient information, and said analysis from the remote treatment equipment;

treating the given patient at the given patient's premises by the appropriate mobile physician in response to the information displayed on the selected portable computer;

inputting orders at the given patient's premises by the appropriate mobile physician into the selected portable computer for the care of the given patient;

wirelessly sending at least one of the orders from the given patient's premises at the time of treating the given patient by the appropriate mobile physician to at least one third party vendor via the selected portable computer for products or services to be provided by the third party vendor;

updating the medical record stored in the local storage of the selected portable computer with the patient information, the analysis and the orders at the given patient's premises at the time of treating given patient;

storing the updated medical record in the local storage of the selected portable computer; and wirelessly uploading the updated medical record to the remote central storage facility.

\* \* \* \* \*

UNITED STATES PATENT AND TRADEMARK OFFICE
CERTIFICATE OF CORRECTION

PATENT NO. : 7,249,036 B2  Page 1 of 1
APPLICATION NO. : 10/934802
DATED : July 24, 2007
INVENTOR(S) : C. Gresham Bayne It is certified that error appears in the above-identified patent and that said Letters Patent is hereby corrected as shown below:

Claim 26, column 20, line 33, delete "prdersf" insert -- orders --.

Claim 33, column 22, line 14, after "of" insert -- said --.

Signed and Sealed this

Eleventh Day of September, 2007

JON W. DUDAS
*Director of the United States Patent and Trademark Office*